(12) United States Patent
Shalaby et al.

(10) Patent No.: US 8,614,291 B2
(45) Date of Patent: Dec. 24, 2013

(54) PHOSPHORYLATED POLYMERS AND CONJUGATES THEREOF

(75) Inventors: Shalaby Wahba Shalaby, Anderson, SC (US); Joel Thomas Corbett, Seneca, SC (US)

(73) Assignee: Poly-Med, Inc., Anderson, SC (US)

(*) Notice: Subject to any disclaimer, the term of this patent is extended or adjusted under 35 U.S.C. 154(b) by 1837 days.

(21) Appl. No.: 11/342,209

(22) Filed: Jan. 27, 2006

(65) Prior Publication Data
US 2006/0127354 A1 Jun. 15, 2006

Related U.S. Application Data

(63) Continuation of application No. 09/762,431, filed as application No. PCT/US99/18146 on Aug. 10, 1999, now abandoned.

(51) Int. Cl.
- C07K 14/00 (2006.01)
- C07K 7/06 (2006.01)
- A61K 38/10 (2006.01)
- A61K 38/16 (2006.01)
- A61K 31/765 (2006.01)
- A61K 31/724 (2006.01)

(52) U.S. Cl.
USPC ......... 530/324; 530/326; 514/1.1; 525/54.1; 424/78.37

(58) Field of Classification Search
None
See application file for complete search history.

(56) References Cited

U.S. PATENT DOCUMENTS

| | | |
|---|---|---|
| 2,729,609 A | 1/1956 | Tess et al. |
| 3,321,555 A | 5/1967 | Lutz et al. |
| 3,538,045 A | 11/1970 | Stewart et al. |
| 3,838,045 A | 9/1974 | Clayfield et al. |
| 4,041,223 A | 8/1977 | Amemiya et al. |
| 4,420,587 A | 12/1983 | Hefner, Jr. |
| 4,487,860 A | 12/1984 | Winner et al. |
| 4,764,604 A | 8/1988 | Muller |
| 4,792,599 A | 12/1988 | Durrani |
| 5,079,337 A | 1/1992 | Dellacherie et al. |
| 5,086,094 A | 2/1992 | Massingill, Jr. |
| 5,162,505 A | 11/1992 | Dean et al. |
| 5,176,907 A | 1/1993 | Leong |
| 5,183,809 A | 2/1993 | Folkman et al. |
| 5,256,765 A | 10/1993 | Leong |
| 5,300,255 A | 4/1994 | Campbell et al. |
| 5,310,879 A | 5/1994 | Tobias et al. |
| 5,476,653 A | 12/1995 | Pitt et al. |
| 5,491,198 A | 2/1996 | Shalaby et al. |
| 5,525,326 A | 6/1996 | Unger |
| 5,536,445 A | 7/1996 | Campbell et al. |
| 5,558,517 A | 9/1996 | Shalaby et al. |
| 5,635,216 A | 6/1997 | Thompson |
| 5,654,422 A | 8/1997 | Hirsenkorn |
| 5,672,659 A * | 9/1997 | Shalaby et al. .............. 525/54.1 |
| 5,686,540 A | 11/1997 | Kakizawa |
| 5,725,881 A | 3/1998 | Buchholz et al. |

FOREIGN PATENT DOCUMENTS

| | | |
|---|---|---|
| EP | 0 326 148 A | 8/1989 |
| EP | 0 375 659 A | 6/1990 |
| EP | 0 386 757 A2 | 9/1990 |
| EP | 0 407 617 A | 1/1991 |
| EP | 0 449 249 A | 10/1991 |
| EP | 0 483 429 A1 | 5/1992 |
| EP | 0 722 966 A | 7/1996 |
| GB | 1 350 225 A | 4/1974 |
| GB | 2 145 422 A | 3/1985 |
| WO | 96 00760 A | 1/1996 |
| WO | 96 31220 A | 10/1996 |
| WO | 97 19948 A | 6/1997 |

OTHER PUBLICATIONS

R.L. Shogren, "Complexes of starch with ...", Carb. Polymers, vol. 22, 1993;93-98 XP000881303.
Database WPI, Derwent Publications Ltd., London, GB; AN 1984-210427[25], XP002140521 & JP 59 122416 A (Lion Corp), Jul. 14, 1984 abstract.
Database WPI, Derwent Publications Ltd., London, GB; AN 1997-063618[06] XP002140522 & KR 9 502 607 B (Samyang Co Ltd) abstract.
Patent Abstracts of Japan, vol. 13, No. 95, Mar. 6, 1989 & JP 63 273679 A (Bio Material Yunibaasu:KK), Nov. 10, 1988, abstract.
Tseng et al., "Effects of poly (D,L-Lactide) addition to ...", J.Bioact. Compat.Polym., vol. 4, No. 2, 1989;101-109, XP000915928.
Tseng et al., "Medical applications of ...", Jino Zoki, vol. 18, No. 1, 1989;409-413, XP000915929.
Shalaby, S.W. et al., J. Polym.Sci., Polym. Chem.Ed.,12,2917-2925 (1974).
Shalaby, S.W. et al., J. Polym.Sci., Polym. Chem.Ed.,13, 669-679 (1975).
Shalaby, S.W. et al., J. Polym.Sci., Polym. Chem.Ed.,14, 2675-2687 (1976).
Koch, P.J. et al., J. Appl. Polym.Sci., 19, 227-234, (1975).
Mao, H.Q. et al., Proceed.Ont'i.Symp. Control.Rel.Bioact.Mater., Controlled Release Society, Inc., 25, (1998), pp. 203.

* cited by examiner

*Primary Examiner* — Julie Ha
(74) *Attorney, Agent, or Firm* — McCormick, Paulding & Huber LLP

(57) ABSTRACT

The present invention is directed to absorbable polyesters comprising one or more monophosphate functionality; a conjugate comprising the foregoing polyester and a peptide and/or a bioactive agent; microparticles comprising an absorbable polyester; a conjugate comprising the microparticles and a peptide and/or a bioactive agent; an acylated or alkylated polysaccharide having one or more monophosphate functionality; a conjugate comprising the acylated or alkylated polysaccharide and a peptide and/or a bioactive agent; and pharmaceutical compositions thereof.

6 Claims, No Drawings

PHOSPHORYLATED POLYMERS AND CONJUGATES THEREOF

This application is a continuation (and claims the benefit of priority under 35 USC 120) of U.S. patent application Ser. No. 09/762,431, filed May 22, 2001 now abandoned, which is the national phase application under 35 U.S.C. §371 of PCT application serial number PCT/US99/18146, with an international filing date of Aug. 10, 1999, which claims priority to U.S. patent application Ser. No. 09/131,472, with a filing date of Aug. 10, 1998, now abandoned, which claims the benefit of U.S. Application No. 60/095,875, with a filing date of Aug. 10, 1998, now abandoned.

BACKGROUND OF THE INVENTION

The present invention is directed to absorbable polyesters comprising one or more monophosphate functionality; a conjugate comprising the foregoing polyester and a peptide and/or a bioactive agent; microparticles comprising an absorbable polyester; a conjugate comprising the microparticles and a peptide and/or a bioactive agent; an acylated or alkylated polysaccharide having one or more monophosphate functionality; a conjugate comprising the acylated or alkylated polysaccharide and a peptide and/or a bioactive agent; and pharmaceutical compositions thereof.

Phosphorous-containing heterochain polymers have been cited in the patent and technical literature in conjunction with (1) flame-retardant and/or hydrophilic polyamides (Shalaby, S. W., et al., J. Polym. Sci., Polym. Chem. Ed., 12, 2917 (1974); Shalaby, S. W., et al., J. Polym. Sci., Polym. Chem. Ed., 13, 669 (1975); Shalaby, S. W., et al., J. Polym. Sci., Polym. Chem. Ed., 14, 2675 (1976); Shalaby, S. W. and McCaig, S., U.S. Pat. No. 5,491,198; Shalaby, S. W. and Rogers, K. R., U.S. Pat. No. 5,558,517); (2) flame-retardant polyesters (Heffner, R. E., U.S. Pat. No. 4,420,587; Koch, P. J., et al., J. Appl. Polym. Sci., 19, 227 (1975); Japanese Pat. 51-40432); (3) flame-retardant polyurethanes and epoxy resins (German Patent DE 1,292,862, U.S. Pat. No. 3,321,555); (4) thermally stable polyesters with chain end-groups reacted with phosphonyl thiocyanate (U.S. Pat. No. 3,838,045); (5) phosphorylated cellulose as a cation-exchanger (DD 286600); and (6) phosphorylated polyesters as semiconducting materials (SU, 672878). However, there is no disclosure in the art of incorporation of phosphate groups at available hydroxy end-group sites of absorbable polyesters, which sites are typically present at one or two terminals of the chain. This is not surprising since conditions of chemical reactions known for hydroxy group phosphorylation could cause hydrolysis of the highly reactive absorbable polyester chains. Meanwhile, there has been great interest in developing carboxyl-bearing absorbable polyesters for use in forming conjugates with bioactive polypeptides as controlled release systems therefor (Shalaby, S. W., et al., U.S. Pat. No. 5,672,659).

Therefore, there is an incentive to make directly phosphorylated absorbable polyesters without significantly causing chain degradation to obtain novel controlled release systems.

SUMMARY OF THE INVENTION

In one aspect, the present invention is directed to an absorbable polyester with at least one monophosphate functionality per absorbable polyester chain. A preferred embodiment of the immediately foregoing absorbable polyester is where the polyester chain comprises one or more monomers selected from the group consisting of L-lactic acid, D-lactic acid, DL-lactic acid, malic acid, citric acid, tartaric acid, ε-caprolactone, ε-caproic acid, alkylene oxalate, cycloalkylene oxalate, alkylene succinate, β-hydroxybutyrate, glycolide, glycolic acid, L-lactide, D-lactide, DL-lactide, meso-lactide, trimethylene carbonate, p-dioxanone, 1,5-dioxepan-2-one and 1,4-dioxepan-2-one and any optically active isomers, racemates, or copolymers thereof. A more preferred embodiment of the foregoing invention is where the absorbable polyester further comprises one or more polyethylene glycol segments covalently linked to the polyester. A further aspect of the foregoing invention, this invention is directed to a conjugate comprising the foregoing absorbable polyester and a peptide and/or a bioactive agent, where the peptide and bioactive agent have at least one interactive amino group, wherein the monophosphate functionality forms a linkage with the amino group. A preferred embodiment of the foregoing conjugate is where the peptide is selected from the group consisting of p-Glu-His-Trp-Ser-Tyr-D-Trp-Leu-Arg-Pro-Gly-NH$_2$, H-β-D-Nal-Cys-Tyr-D-Trp-Lys-Val-Cys-Thr-NH$_2$ where the two Cys are bonded by a disulfide bond, N-hydroxyethylpiperazinyl-acetyl-D-Phe-Cys-Tyr-D-Trp-Lys-Abu-Cys-Thr-NH$_2$ where the two Cys are bonded by a disulfide bond and N-hydroxyethylpiperazinyl-ethylsulfonyl-Phe-Cys-Tyr-D-Trp-Lys-Abu-Cys-Thr-NH$_2$ where the two Cys are bonded by a disulfide bond, or a pharmaceutically acceptable salt thereof.

In another aspect, the present invention is directed to a conjugate comprising an absorbable polyester with at least one monophosphate functionality per absorbable polyester chain and a peptide and/or a bioactive agent, where the peptide and bioactive agent have at least one interactive amino group, wherein the monophosphate functionality forms a linkage with the amino group. A preferred conjugate is wherein the peptide is selected from the group consisting of p-Glu-His-Trp-Ser-Tyr-D-Trp-Leu-Arg-Pro-Gly-NH$_2$, H-β-D-Nal-Cys-Tyr-D-Trp-Lys-Val-Cys-Thr-NH$_2$ where the two Cys are bonded by a disulfide bond, N-hydroxyethylpiperazinyl-acetyl-D-Phe-Cys-Tyr-D-Trp-Lys-Abu-Cys-Thr-NH$_2$ where the two Cys are bonded by a disulfide bond and N-hydroxyethylpiperazinyl-ethylsulfonyl-Phe-Cys-Tyr-D-Trp-Lys-Abu-Cys-Thr-NH$_2$ where the two Cys are bonded by a disulfide bond, or a pharmaceutically acceptable salt thereof.

In another aspect, the present invention is directed to a solid absorbable microparticle which comprises an absorbable polyester with at least one monophosphate functionality per absorbable polyester chain and having a surface, wherein more than one percent of the monophosphate functionality resides on the surface of the absorbable microparticle. A further aspect of the present invention is a conjugate comprising the immediately foregoing absorbable microparticle and a peptide and/or a bioactive agent, where the peptide and bioactive agent have at least one interactive amino group, wherein the monophosphate functionality on the surface of the absorbable microparticle forms a linkage with the amino group. A preferred embodiment of the immediately foregoing conjugate is the conjugate wherein the peptide is selected from the group consisting of p-Glu-His-Trp-Ser-Tyr-D-Trp-Leu-Arg-Pro-Gly-NH$_2$, H-β-D-Nal-Cys-Tyr-D-Trp-Lys-Val-Cys-Thr-NH$_2$ where the two Cys are bonded by a disulfide bond, N-hydroxyethylpiperazinyl-acetyl-D-Phe-Cys-Tyr-D-Trp-Lys-Abu-Cys-Thr-NH$_2$ where the two Cys are bonded by a disulfide bond and N-hydroxyethylpiperazinyl-ethylsulfonyl-Phe-Cys-Tyr-D-Trp-Lys-Abu-Cys-Thr-NH$_2$ where the two Cys are bonded by a disulfide bond, or a pharmaceutically acceptable salt thereof.

In yet another aspect, the present invention is directed to an acylated or alkylated absorbable polysaccharide, having one or more terminal monophosphate functionality per molecule.

A preferred embodiment of the immediately foregoing is where the absorbable polysaccharide is an acylated gamma-cyclodextrin. A further aspect of the foregoing is a conjugate comprising the alkylated or acylated absorbable polysaccharide having one or more terminal monophosphate functionality per molecule and a peptide and/or a bioactive agent, where the peptide and bioactive agent have at least one interactive amino group, wherein the monophosphate functionality forms a linkage with the amino group. A preferred embodiment of the immediately foregoing conjugate is a conjugate where the peptide is selected from the group consisting of p-Glu-His-Trp-Ser-Tyr-D-Trp-Leu-Arg-Pro-Gly-NH$_2$, H-β-D-Nal-Cys-Tyr-D-Trp-Lys-Val-Cys-Thr-NH$_2$ where the two Cys are bonded by a disulfide bond, N-hydroxyethylpiperazinyl-acetyl-D-Phe-Cys-Tyr-D-Trp-Lys-Abu-Cys-Thr-NH$_2$ where the two Cys are bonded by a disulfide bond and N-hydroxyethylpiperazinyl-ethylsulfonyl-Phe-Cys-Tyr-D-Trp-Lys-Abu-Cys-Thr-NH$_2$ where the two Cys are bonded by a disulfide bond, or a pharmaceutically acceptable salt thereof.

In still another aspect, the present invention is directed to a pharmaceutical composition comprising one or more of the conjugates described herein.

In a further aspect, the present invention is directed to an absorbable polymer with at least one monophosphate functionality for use as an acidic excipient of a cyanoacrylate composition.

In another further aspect, the present invention is directed to a method for making a low melting phosphorylated-hydroxyl-bearing polyester having 1% to 60% crystallinity, which comprises reacting a hydroxyl-bearing polyester with an excess of pyrophosphoric acid to yield the phosphorylated-hydroxyl-bearing polyester.

In another further aspect, the present invention is directed to a method for making a phosphorylated-acylated cyclodextrin, which comprises reacting an acylated cyclodextrin with an excess of pyrophosphoric acid to yield the phosphorylated-acylated cyclodextrin.

In another further aspect, the present invention is directed to a method for making a phosphorylated-alkylated cyclodextrin, which comprises reacting an alkylated cyclodextrin with an excess of pyrophosphoric acid to yield the phosphorylated-alkylated cyclodextrin.

In another further aspect, the present invention is directed to a method for making phosphorylated microparticles, which comprises reacting a hydroxyl-bearing microparticle with excess pyrophosphoric acid to yield the phosphorylated microparticles.

In another further aspect, the present invention is directed to a method of making an acylated-phosphorylated polysaccharide, which comprises reacting a polysaccharide concurrently with a heated mixture of pyrophosphoric acid and an acylating agent to yield the acylated-phosphorylated polysaccharide. A preferred method of the foregoing method is where the polysaccharide is cyclodextrin and the acylating agent is propionic anhydride or acetic anhydride. The reaction can be conducted between about room temperature to about 100° C.

In another further aspect, the present invention is directed to a phosphorylated-grafted-acylated cyclodextrin having one or more monophosphate functionality.

In another further aspect, the present invention is directed to a method of preparing phosphorylated-grafted-acylated cyclodextrin that has been grafted with a heterocyclic monomer, including those used for the preparation of absorbable polymers, e.g., lactide, glycolide, trimethylene carbonate and/or ε-caprolactone, which method comprises heating a monomer with an acylated cyclodextrin in the presence of a catalytic amount of stannous octoate for about 2-24 hours at about 100° C. to 200° C. to form a reaction mixture comprising grafted-acylated cyclodextrin; dissolving the reaction mixture comprising the grafted-acylated cyclodextrin in acetone to make an acetone solution; precipitating the acetone solution in ice water to form a precipitate; isolating the precipitate; drying the precipitate to give a dried precipitate; and reacting the dried precipitate with an excess of pyrophosphoric acid to yield phosphorylated-grafted-acylated cyclodextrin.

In another further aspect, the present invention is directed to a conjugate comprising a peptide and/or a bioactive agent and a phosphorylated-grafted-acylated cyclodextrin, where the peptide and bioactive agent have at least one interactive amino group and the monophosphate group forms a linkage with the amino group.

The term "grafted" refers to a polyester graft originating from a heterocyclic monomer, such as lactide, glycolide, trimethylene carbonate and/or ε-caprolactone.

The term "absorbable" means that a water insoluble material such as a polymer which undergoes chain dissociation in the biological environment to water soluble by-products as a function of time and leaves hardly any residue at the site of implant or administration.

The instant application denotes amino acids using the standard three letter abbreviations known in the art, for example Ala=alanine.

The term "microparticle" as used herein, refers to the particles of absorbable polyester, which are preferably in essentially spherical form.

The term "monophosphate functionality" means that the polymer chain is covalently linked to phosphoric acid by a single phosphate bond leaving two additional acidic —OH groups available for conjugation or neutralization as depicted in the following structure: polyester-CHR—O—P(O)(OH)$_2$, where R is, for example H or CH$_3$.

The term "peptide" is meant to include peptides, polypeptides and proteins. Examples of peptides include but are not limited to growth hormone releasing peptide (GHRP), leutenizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), encephalon, endothelin, calcitonin gene releasing peptide (CRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH, growth hormone, erythropoietin, granulocyte-colony stimulating factor, granulocyte-macrophage-colony stimulating factor, interferons, the LHRH analog p-Glu-His-Trp-Ser-Tyr-D-Trp-Leu-Arg-Pro-Gly-NH$_2$ (Peptide A), the somatostatin analog H-β-D-Nal-Cys-Tyr-D-Trp-Lys-Val-Cys-Thr-NH$_2$ where the two Cys are bonded by a disulfide bond (Peptide B), N-hydroxyethylpiperazinyl-acetyl-D-Phe-Cys-Tyr-D-Trp-Lys-Abu-Cys-Thr-NH$_2$ where the two Cys are bonded by a disulfide bond, or N-hydroxyethylpiperazinyl-ethylsulfonyl-Phe-Cys-Tyr-D-Trp-Lys-Abu-Cys-Thr-NH$_2$ where the two Cys are bonded by a disulfide bond (Peptide C), and analogs and fragments thereof or a pharmaceutically acceptable salt thereof.

The term "bioactive agent" is meant to include any chemical compound, including peptides, that can be administered to a patient for therapeutic or prophylactic purposes and, thus, includes pharmaceuticals.

The term "interactive amino group" refers to an amino group that is capable of chemically reacting with another chemical functionality, such as a hydroxy group of a monophosphate moiety.

The term "linkages" refers to chemical bonds, which can be ionic and/or covalent in nature, between the entities named.

The phrase "terminal monophosphate functionality per absorbable polyester chain" indicates that each end of the polyester chain can have a monophosphate functionality.

Members of the monophosphate family of polyesters which are miscible in cyanoacrylate esters can be used as an acidic excipient in absorbable tissue adhesive compositions comprising alkoxyalkyl cyanoacrylates. The acidic functionality of these polyesters can stabilize the cyanoacrylate in the presence of trace amounts of environmental contaminants that are basic in nature.

The term "low melting polyester" means that the polyester has a melting range of between about 25° C. to 120° C.

The term "crystallinity" refers to the fraction of the solid that exhibits 3-dimensional order that is maintained until the material is heated to a temperature at or above the melting temperature where the material converts to a liquid.

DETAILED DESCRIPTION

The present invention is directed to monophosphate analogues of several types of hydroxylic oligomers and polymers, which can be liquids, amorphous solids, or crystalline materials at room temperature. The free —P(O)(OH)$_2$ functionality of the phosphorylated derivatives of the oligomeric and polymeric systems is capable of conjugating, ionically and/or covalently, with basic amine groups of bioactive agents including peptides and proteins. The phosphorylation can be conducted on molten polyester or solid microparticulate polyesters and pre-modified or in situ modified polysaccharides, such as partially acylated cyclodextrins. The phosphorylated substrates of this invention are used to form novel ionic conjugates with amino-acids, polypeptides, and proteins or any organic compound that has at least one available interactive amine group.

The hydroxylic oligomers and polymers that are the subject of this invention include hydroxy terminated polyesters (HTPE) and acylated or alkylated cyclodextrins. The polyesters (HTPE) can be prepared by the ring opening polymerization of lactones (such as glycolide, lactide, ε-caprolactone, p-dioxanone) and/or cyclic carbonate (such as trimethylene carbonate) in the presence of an inorganic or organometallic catalyst (such as stannous octoate) and a hydroxyl-bearing initiator (such as 1,6-hexanediol, 1,3-propanediol and diethylene glycol) under conditions that are commonly used in the art for ring opening polymerization (see Shalaby, S. W., et al., "Absorbable Polyesters" in *Biomedical Polymers Designed to Degrade*, Chapter 1, Shalaby, S. W. Ed. Hansen Publ., NY 1994). The resulting polyesters, copolyesters, or copolyester-carbonates can be in the form of a liquid, amorphous or highly crystalline materials having at least one hydroxyl group per polymeric chain. Highly crystalline solids of polyesters of this invention can be reduced in size to form microparticles having an average diameter of 0.1 to 100 microns. Other hydroxylic oligomers and polymers include derivatives of oligosaccharide, such as acylated or alkylated cyclodextrins, having at least one hydroxylic group per molecule. These derivatives can be phosphorylated directly or grafted with a polyester, copolyester, or copolyester-carbonate chains, such as those described above for the hydroxy-terminated polyesters.

Conversion of the hydroxyl-bearing oligomers and polymers of the types described herein is achieved by phosphorylating the hydroxyl groups thereof, using reactive phosphoric acid derivatives, such as pyrophosphoric acid. Stoichiometric or excess amounts of the phosphorylating agent is used. The reaction is carried out with or without an unreactive solvent and at a temperature ranging from about 10° C. to 150° C. for a period of several minutes to several hours, depending on the chemical structure of the reacting substrate. At the conclusion of the reaction, the product is fractionated to remove any excess reagent and by-products. Upon using pyrophosphoric acid, the resulting reaction mixture is dissolved in a water-miscible solvent, such as acetone. The acetone solution is then added to stirring ice-water. This is followed by isolating the solid phosphorylated product by centrifugation or filtration. After rinsing the product sufficiently, it is dried under reduced pressure. When crystalline microparticulate hydroxylic substrates are used, the reaction conditions can be adjusted to insure that the microparticles maintain their original dimensions after being phosphorylated. The reaction of the microparticulate can be conducted with or without the use of a liquid non-reactive organic medium. Pyrophosphoric acid is a typical example of the reactive acid derivatives that can be used to insert —O—P(O)(OH)$_2$ functionality into the hydroxyl-bearing substrate. Examples of other phosphorylating agents that can be used in the present invention include methyl monophosphate, ethyl monophosphate and phenyl monophosphate.

To form conjugates of the different polymer monophosphates, the individual polymer monophosphate is dissolved or suspended in a suitable medium "A", such as water or a mixture of water and acetonitrile, and allowed to interact with a basic bioactive agent present in an aqueous solution that is miscible in "A". Depending on the chemistry of the bioactive agent, a basic inorganic reagent may be required to present the bioactive agent in its free basic form. In case of a peptide salt, such as a peptide acetate, an inorganic base, such as sodium bicarbonate, can be used to abstract the acetate ions from the peptide and allow its free base to conjugate, ionically and/or covalently, with the monophosphate group of the oligomeric or polymeric substrates.

A microparticle of the present invention is made by micronizing a polymer by initially grinding it using a Knife-grinder. The polymer is then micronized in an Aljet Micronizer using a pressurized dry nitrogen stream. The mean particle diameter size is analyzed in a Malvern Mastersizer/E using a volume distribution model and 200/5 cS silicone oil as dispersant.

The conjugate microparticles of this invention can be administered to a patient via administration routes well known to those of ordinary skill in the art, such as parenteral administration, oral administration or topical administration. Preferably, it is administered as a powder or a suspension via intranasal route or as an inhalant through the pulmonary system. When it is administered parenterally it is preferable that it is administered as a dispersion in an isotonic aqueous medium or in a non-aqueous, absorbable gel-forming liquid polyester as described in U.S. Pat. No. 5,612,052, the contents of which are incorporated herein by reference. The formulations comprising conjugate microparticles of the present invention can also include a variety of optional components. Such components include, but are not limited to, surfactants, viscosity controlling agents, medicinal agents, cell growth modulators, dyes, complexing agents, antioxidants, other polymers such as carboxymethyl cellulose, gums such as guar gum, waxes/oils such as castor oil, glycerol, dibutyl phthalate and di(2-ethylhexyl)phthalate and the like.

If used, such optional components comprise from about 0.1% to about 20%, preferably from about 0.5% to about 5% of the total formulation.

The effective dosages of a conjugate microparticles of the present invention to be administered to a patient can be determined by the attending physician or veterinarian and will be dependent upon the proper dosages contemplated for the peptide and/or bioactive agent conjugated in the microparticles. Such dosages will either be known or can be determined by one of ordinary skill in the art.

The disclosure of each of the references cited herein are incorporated herein by reference.

The following examples are provided for illustrative purposes and the teachings therein are not meant to limit the scope of the present invention.

EXAMPLE 1

Preparation of a Hydroxy-Terminated Polyester

CEG-1 was made from caprolactone (137.3 g, 1.204 mole) and diethylene glycol (12.7 g, 0.12 mole) using stannous octoate (Sigma Chemical Co., St. Louis, Mo.), as a catalyst, at 5000:1 mole ratio of monomer/catalyst (1.3 ml of 0.2M toluene solution). The flask was charged and set up with a mechanical stirrer. The reactants were heated for about 12 hours at about 150° C. under dry argon. The polymer was isolated and purified by precipitating an acetone solution of the reaction mixture in ice water. The resulting polymer was isolated, dried, and then analyzed for identity composition, molecular weight, and thermal properties using IR, NMR, GPC, and DSC, respectively. Unreacted monomer was distilled under reduced pressure at about 120° C.

Substituting 1,3-propanediol for diethylene glycol at different monomer/initiator ratios, a number of hydroxy terminated polymers, having a range of molecular weights, were prepared according to the procedure described for Example 1. These include CPD-1 and CPD-2, which are based on ε-caprolactone and 1,3-propanediol.

Using a mixture of 70/30 l-lactide/glycolide, 85/15 dl-lactide/glycolide, 70/30 l-lactide/glycolide or 80/20 l-lactide/dl-lactide, the respective copolymers, denoted PDLG-1, PDLG-2, PD-100, and PD-101, respectively, were produced substantially according to the procedure described for Example 1 under similar reaction conditions and variable amounts of 1,3-propanediol to achieve the desired molecular weights (Mn) ranging from 2 to 20 kDa.

EXAMPLE 2

Preparation of Phosphorylated Polyesters

CEG-1-Phos-5 was made from CEG-1 (from Example 1) and pyrophosphoric acid without the aid of a solvent using a 4:1 mole ratio of pyrophosphoric acid (1.3 g) to CEG-1 (5.0 g). The foregoing reaction mixture was allowed to react for about 80 minutes at room temperature. The resulting product was dissolved in 30 ml acetone and precipitated in ice water. The polymer was isolated and dried under reduced pressure and then analyzed as described in Example 1. In addition, the phosphorous content was determined by elemental analysis. The equivalent weight of the phosphorylated product was determined by acidimetry.

Following the foregoing procedure for making CEG-1-Phos-5, two other batches of phosphorylated CEG-1 were prepared, namely CEG-1-Phos-6 and CEG-1-Phos-7. Similarly, CPD-2 was phosphorylated to produce CPD-2-Phos-1 and copolymers, PLDG-1, PDLG-2, PD-100, and PD-101 to produce PLDG-1-Phos-1, PDLG-1-Phos-1, PD-100-Phos-1 and PD-101-Phos-1, respectively, all substantially according to the procedure for making CEG-1-Phos-5.

EXAMPLE 3

Preparation of Phosphorylated Polyester/Polypeptide Conjugates

CON-P3 was made from Peptide A and CEG-1-Phos-5A (another batch of CEG-1-Phos-5). Thus, CEG-1-Phos-5A (0.9974 g) was dissolved in 10 ml of acetonitrile. This solution was filtered through a syringe filter in order to remove traces of insoluble polymer particles. Peptide A (199 mg) was dissolved in 2 ml of water. Based on the acetate content of the Peptide A, 25 mg of sodium carbonate was added to the polymer solution in acetonitrile to exchange with the acetate in the peptide. Peptide A solution was then added to the polymer solution dropwise. After the entire peptide solution was added over about a ten minute interval, the resulting solution was allowed to stir for about 0.5 hour. The solution was then precipitated into ice cold salt water and centrifuged to collect the product. The latter was rinsed with distilled water and recentrifuged. The product was dried under vacuum. The resulting conjugate was analyzed for its peptide content using elemental analysis for nitrogen.

Following a similar procedure as described for Example 3, the conjugates described in Table I were prepared from the designated individual peptides and phosphorylated polyesters at the noted ratios and precipitation media (PM, water or isopropyl alcohol).

EXAMPLE 4

Preparation of Crystalline Hydroxy-Terminated Polyglycolide Microparticles

PDGLY-1 was made as a solid crystalline material using about 25:1 mole ratio of glycolide to 1,3-propanediol. Glycolide (200 g, 1.724 mole) was melted in a flame-dried flask under argon and 1,3-propanediol (5.249 g, 69.1 mmole) was added. Stannous octoate (0.575 ml of 0.2M in toluene) was placed in the flask containing the molten reactants and the temperature was raised to about 160° C. After approximately 30 minutes, the polymerization was concluded and the temperature was lowered to about 110° C. Unreacted monomer was removed by distillation at about 120° C. under reduced pressure. The product was then ground and micronized as described hereinabove.

In a similar manner as the procedure for Example 4, PD-102 was made from a 15/1 mixture of glycolide and 2,3-propanediol.

EXAMPLE 5

Preparation of Surface Phosphorylated Polyglycolide Microparticles

PDGLY-1-Phos-2 was made by melting 9.7 g of pyrophosphoric acid at about 60° C. and adding, while stirring under dry argon, 4.4 g of PDGLY-1. The reaction was continued for about three hours at the same temperature. The product was cooled to about 10° C. and then mixed with 20 ml of cold water. The mixture was sonicated for about 5 minutes, washed three times with water, and then dried under reduced pressure. The product was analyzed for its phosphorous content and $T_m$ using elemental analysis and DSC, respectively.

In an analogous manner, PD-102 was converted to PD102-Phos1 substantially according to the procedure for making PDGLY-1-Phos-2.

EXAMPLE 6

Preparation of Typical Polypeptide Conjugates Using Phosphorylated Polyglycolide Microparticles PICP3 was made from PDGLY1-Phos2 and Peptide B (50 mg) dissolved in 2 ml of a 50:50 acetonitrile/water mixture. A 20 μl aliquot of the peptide solution was removed as a control sample. PDGLY1-Phos2 (502 mg) was added to the vial containing the rest of the peptide solution and sonicated for about five minutes and then stirred for about two hours. The product was isolated by centrifugation and then dried under reduced pressure. The supernatant liquid was analyzed by HPLC to determine the amount of peptide bound to the powder. HPLC results indicated that 6.7%, by weight, of peptide was bound. The peptide content was found to be 7.2% by elemental analysis for nitrogen.

In an analogous manner as the foregoing procedure, PD102-Phos1 was conjugated with Peptide B to produce PICP-4.

EXAMPLE 7

Preparation of Endo-Chain Carboxylated 85/15 Poly(dl-lactide-co-glycolide) (TR-100)

An 85/15 (molar) mixture of dl-lactide and glycolide was polymerized following essentially the same procedure described in Example 1 but using L-tartaric acid as the initiator (at a molar ratio of 50/1 lactone/tartaric acid) and stannous octoate as a catalyst (at a monomer to catalyst ratio of 5000/1).

EXAMPLE 8

Phosphorylation of TR-100 to Produce TR101-Phos2

The phosphorylation was conducted as described in Example 2, using a mixture of TR-100 (15 g) and pyrophosphoric acid (1.244 g).

EXAMPLE 9

Ionic Conjugation of TR100-Phos1 to Produce CON-P9, CON-P12, and CON-P15

Using a similar procedure to that described for Example 3, Peptide B (373 mg) was reacted with 1.5 g TR100-Phos1 to produce CON-P9. Similarly, CON-P12 was prepared using Peptide A (400 mg) and TR100-Phos1 (2.5 g). In preparing CON-P15, cold 2-propanol was used as the precipitating medium producing a conjugate based on Peptide B (400 mg) and TR100-Phos1 (2.5 g).

EXAMPLE 10

Preparation of a Phosphorylated Derivative of Gamma Cyclodextrin (GCD-Phos3)

An aliquot of γ-cyclodextrin (20.0 g) was mixed in a pre-dried flask with 46.23 g of propionic anhydride and 16.46 g of pyrophosphoric acid in a dry nitrogen environment. The reactants were heated at about 45° C. while being mixed for approximately 0.5 hour. The mixture was cooled and then precipitated into ice cold distilled water. The product was isolated and then dried under reduced pressure. Analysis revealed that the material has 0.43% phosphorous by weight and an equivalent weight of 1251.

EXAMPLE 11

Preparation of a Typical Polypeptide Conjugate of Phosphorylated γ-Cyclodextrin Derivative A typical derivative such as GCD-Phos3 (1.7 g) was conjugated with a peptide (e.g., Peptide B, 300 mg) as described for the conjugate preparation in Example 3, to produce CONG-P100.

EXAMPLE 12

Preparation of a Tissue Adhesive Composition

The phosphorylated polyester from Example 2 (0.5 g) was dissolved in methoxypropyl cyanoacrylate (9.5 g) and the resulting liquid composition was stored at room temperature in an untreated (not washed with acid) glass vial for several days and showed no signs of polymerization (as indicated by no visible change in viscosity). Applying such tissue adhesive composition to a moist goat skin led to the formation of a compliant (flexible) tissue adhering film in about one minute.

TABLE I

Experimental Data for the Preparation of Typical Conjugates

| Conjugate | Phosphorylated Polyester | Peptide | Phosphorylated Polyester/Peptide | PM* |
|---|---|---|---|---|
| CON-P1 | CEG1-Phos5 | B | 1.5 g/373 mg | $H_2O$ |
| CON-P7 | CEG1-Phos6 | B | 2.0 g/300 mg | $H_2O$ |
| CON-P10 | CEG1-Phos7 | A | 3.0 g/758 mg | $H_2O$ |
| CON-P11 | CEG1-Phos7 | A | 1.5 g/190 mg | IPA |
| CON-P13 | CPD2-Phos1 | A | 3.0 g/700 mg | $H_2O$ |
| CON-P14 | CPD2-Phos1 | A | 3.0 g/500 mg | IPA |
| CON-P4 | PDLG2-Phos1B | B | 1.5 g/373 mg | $H_2O$ |
| CON-P5 | PDLG2-Phos1B | C | 2.0 g/333 mg | $H_2O$ |
| CON-P6 | PDLG2-Phos1B | A | 1.5 g/300 mg | $H_2O$ |
| CON-P15 | TR100-Phos1 | A | 2.5 g/400 mg | IPA |
| CON-P8 | PD100-Phos1 | B | 1.5 g/373 mg | $H_2O$ |
| CON-P16 | PD101-Phos1 | B | 1.5 g/373 mg | $H_2O$ |
| PIC-P3 | PDGLY1-Phos2 | B | 0.5 g/50 mg | N/A |
| PIC-P4 | PD102-Phos1 | B | 0.5 g/50 mg | N/A |
| CONG-P100 | GCD-Phos3 | B | 1.7 g/300 mg | $H_2O$ |

*PM = Precipitation medium

TABLE II

Composition and Properties of Conjugates and Their Precursors
Analytical Data

| Polyester Number | Yield % | GPC Mn | GPC Mw | DSC Tm | Eq. Wt.* | Phos. % | Peptide (%)** |
|---|---|---|---|---|---|---|---|
| TR-100 | 81.2 | 8582 | 22,384 | — | 1333 | | |
| PD-100 | 86.5 | 5205 | $16.3 \times 10^3$ | — | — | — | — |

TABLE II-continued

Composition and Properties of Conjugates and Their Precursors
Analytical Data

| Polyester Number | Yield % | GPC Mn | GPC Mw | DSC Tm | Eq. Wt.* | Phos. % | Peptide (%)** |
|---|---|---|---|---|---|---|---|
| PD-101 | 88.3 | $13.3 \times 10^3$ | $18.6 \times 10^3$ | — | — | — | — |
| PD-102 | 99.1 | — | — | — | — | — | — |
| CEG-1 | 96.0 | 2732 | 3134 | 47.5 | 7395 | | |
| CPD-1 | 91.9 | 2732 | 3595 | N/A | 22,440 | | |
| CPD-2 | 96.6 | 5788 | 8527 | 58.3 | 39,324 | | |
| PDLG-2 | 93.8 | $10 \times 10^3$ | $17 \times 10^3$ | — | — | | |
| PDLG4-1 | 95.0 | 9388 | 13614 | | | | |
| PDGLY-1 | 77.7 | — | — | — | — | | |
| *Phosphorylated Number/Precursor Used* | | | | | | | |
| CPD2-Phos1/CPD-2 | 19.2 | 5376 | $24 \times 10^3$ | 53.6 | 745 | 0.85 | — |
| TR100-Phos1/TR-100 | 81.8 | 9067 | 29,656 | — | 988 | 0.68 | |
| PD100-Phos1/PD-100 | 89.0 | 6108 | 8776 | 39.3 | 1344 | 0.56 | |
| PDLG2-Phos1B/PDLG-2 | 97.2 | 8833 | $14 \times 10^3$ | 46.2 | 2624 | 0.07 | |
| PD101-Phos1/PD-101 | 70.0 | 8535 | 16,188 | — | 1110 | 0.83 | |
| PD102-Phos1/PD-102 | 76.8 | — | — | — | — | 0.98 | — |
| CEG1-Phos5/CEG-1 | 60.3 | 2926 | 3734 | 53.5 | 1339 | 1.11 | |
| CEG1-Phos6/CEG-1 | 69.6 | 4217 | 8825 | 41.4 | 960 | 2.11 | |
| CEG1-Phos7/CEG-1 | 52.0 | 4345 | 8593 | — | 1020 | 1.85 | |
| PDLG1-Phos1/PDLG-1 | 78.1 | 8703 | 12,767 | — | 2810 | 0.19 | |
| PDGLY1-Phos2/PDGLY-1 | 88.6 | — | — | — | — | 0.60 | |
| GCD-Phos3/GCD | 21.9 | — | — | — | 1251 | 0.43 | |
| *Peptide Number/Precursor Used* | | | | | | | |
| CON-P9/TR100-Phos1 | 43.0 | | | — | | | B (10.96) |
| CON-P12/TR100-Phos1 | 11.8 | | | — | | | A (21.4) |
| CON-P8/PD100-Phos1 | 73 | | | 54.4 | | | B (11.25) |
| CON-P4/PDLG2-Phos1B | 63.2 | | | 53.8 | | | B (4.9) |
| CON-P5/PDLG2-Phos1B | 73.5 | | | 48.0 | | | C (4.7) |
| CON-P6/PDLG2-Phos1B | 78.6 | | | 54.9 | | | A (4.8) |
| CON-P1/CEG1-Phos5 | 63.4 | | | | | | B (18.5) |
| CON-P3/CEG1-Phos5 | 82.3 | | | | | | A (12.8) |
| CON-P7/CEG1-Phos6 | 33 | | | 47.8 | | | B (12.66) |
| CON-P2/PDLG1-Phos1 | 62.4 | | | | | | B (5.4) |
| CON-P11/CEG1-Phos7 | 70.7 | | | | | | A (9.94) |
| CON-P10/CEG1-Phos7 | 6.8 | | | | | | A (5.69) |
| CON-P15/TR100-Phos1 | 72.4 | | | — | | | A (6.2) |
| CON-P13/CPD2-Phos1 | 5.1 | — | — | — | — | — | A (8.78) |
| CON-P14/CPD2-Phos1 | 75.1 | — | — | 57.0 | — | — | A (9.5) |
| CON-P8/PD100-Phos1 | 73 | — | — | 54.4 | — | — | B (11.25) |
| CON-P4/PLG2-Phos1B | 63.2 | — | — | 53.8 | — | — | B (4.9) |
| CON-P5/PLG2-Phos1B | 73.5 | — | — | 48.0 | — | — | C (4.7) |
| CON-P6/PLG2-Phos1B | 78.6 | — | — | 54.9 | — | — | A (4.8) |
| CON-P16/PD101-Phos1 | 61.6 | — | — | — | — | — | B (4.8) |
| PIC-P3/PDGLY1-Phos2 | 74 | — | — | — | — | — | B (7.2) |
| PIC-P4/PD102-Phos1 | 87.2 | — | — | — | — | — | B (5.6) |
| CONG-P100/GCD-Phos3 | 70.3 | — | — | — | — | — | B (4.3) |

*Equivalent weight was determined by titration for acid groups
**Based on elemental analysis for nitrogen.

TABLE III

Release Data

| Conjugate | Analyte Peptide (%) | In Vitro Study, Cumulative % Released at Specific Intervals | | | | | | | In Vivo Release* (ng/ml)/on day | | | | | |
|---|---|---|---|---|---|---|---|---|---|---|---|---|---|---|
| | | Day 5 | Day 10 | Day 15 | Day 20 | Day 25 | Day 30 | Day 40 | 0.25 | 5 | 10 | 15 | 23 | 30 |
| CON-P1 | B (18.5)** | 2.3 | 4.4 | 6.3 | 9.45 | 11.5 | 12.8 | 13.9 | 11.5 | 6.4 | 0.8 | 0.2 | — | — |
| CON-P2 | B (5.4) | 11.9 | 18.7 | 27.4 | 40.1 | 46.8 | 51.0 | 55.3 | — | — | — | — | — | — |
| CON-P3 | A (12.8) | 20.2 | 29.4 | 30.3 | 39.2 | 43.7 | 46.5 | 46.9 | — | — | — | — | — | — |
| CON-P4 | B (4.9) | 11.7 | 18.5 | 25.4 | 30.9 | 36.1 | 39.1 | 42.8 | 12.8 | 1.9 | <0.1 | — | — | — |
| CON-P5 | C (4.7) | 1.6 | 2.3 | 2.7 | 3.0 | 3.4 | 3.8 | 4.0 | 2.04 | 0.18 | 0.23 | 0.56 | 0.15 | |
| CON-P6 | A (4.8) | 2.8 | 3.4 | 3.4 | 4.1 | 4.6 | — | — | — | — | — | — | — | — |
| CON-P7 | B (12.66) | 3.2 | 4.9 | 6.2 | — | — | — | — | — | — | — | — | — | — |
| CON-P8 | B (11.25) | 14.9 | 19.4 | 24.7 | — | — | — | — | 15.4 | 8.0 | 4.6 | 1.0 | 0.2 | — |
| CON-P9 | B (10.96) | 10.8 | 13.5 | 19.3 | — | — | — | — | 9.6 | 3.7 | 3.0 | <0.1 | — | — |
| CON-P10 | A (5.7) | | | | | | | | — | — | — | — | — | — |
| CON-P11 | A (9.9) | | | | | | | | | | | | | |
| CON-P12 | A (21.4) | 37.0 | 55.4 | 60.9 | 62.4 | | | | — | — | — | — | — | — |

TABLE III-continued

Release Data

| Conjugate | Analyte Peptide (%) | In Vitro Study, Cumulative % Released at Specific Intervals | | | | | | | In Vivo Release* (ng/ml)/on day | | | | | |
|---|---|---|---|---|---|---|---|---|---|---|---|---|---|---|
| | | Day 5 | Day 10 | Day 15 | Day 20 | Day 25 | Day 30 | Day 40 | 0.25 | 5 | 10 | 15 | 23 | 30 |
| CON-P13 | A (8.8) | — | — | | | | | | — | — | — | — | — | — |
| CON-P14 | A (9.5) | 27.8 | 38.0 | | | | | | — | — | — | — | — | — |
| CON-P15 | A (5.25) | 16.6 | 19.9 | — | — | — | — | — | — | — | — | — | — | — |
| CON-P16 | B (4.8) | — | — | — | — | — | — | — | — | — | — | — | — | — |
| PIC-P3 | B (6.7) | 2.1 | 2.9 | 3.2 | 3.6 | 3.8 | 4.1 | 5.8 | — | — | — | — | — | — |
| PIC-P4 | B (6.12) | | | | | | | | — | — | — | — | — | — |
| CONG-P100 | B (4.3) | 5.7 | 12.1 | 12.8 | — | — | | | — | — | — | — | — | — |

*The release study was conducted in rats and the release profile was monitored by determining the peptide concentration in serum at different time periods using radio immunoassay.
**Only half the usual dose was administered to rats.

What is claimed is:

1. A solid, ionic conjugate of a peptide and an absorbable polyester comprising polyester chains, wherein:
   i) the polyester is covalently linked by a single phosphate bond to at least one phosphoric acid molecule per absorbable polyester chain such that the phosphoric acid has two free phosphate groups available for conjugation;
   ii) the peptide is p-Glu-His-Trp-Ser-Tyr-D-Trp-Leu-Arg-Pro-Gly-NH$_2$, or a pharmaceutically acceptable salt thereof; and
   iii) an amino group of the peptide forms an ionic bond with a free phosphate group of the at least one phosphoric acid.

2. A solid absorbable microparticle which comprises the conjugate of claim 1, wherein more than one percent of the phosphoric acid molecules reside on the surface of the absorbable microparticle.

3. The conjugate according to claim 1, wherein the polyester chain comprises one or more monomers selected from the group consisting of L-lactic acid, D-lactic acid, DL-lactic acid, malic acid, citric acid, tartaric acid, ε-caprolactone, ε-caproic acid, alkylene oxalate, cycloalkylene oxalate, alkylene succinate, β-hydroxybutyrate, glycolide, glycolic acid, L-lactide, D-lactide, DL-lactide, meso-lactide, trimethylene carbonate, p-dioxanone, 1,5-dioxepan-2-one and 1,4-dioxepan-2-one and any optically active isomers, racemates, or copolymers thereof.

4. The conjugate according to claim 1 further comprising one or more polyethylene glycol segments covalently linked to said polyester.

5. A pharmaceutical composition comprising an ionic conjugate according to claim 1 and a pharmaceutically acceptable carrier matrix.

6. The conjugate according to claim 3 further comprising one or more polyethylene glycol segments covalently linked to said polyester.

* * * * *